(12) United States Patent
Vana et al.

(10) Patent No.: US 8,636,885 B2
(45) Date of Patent: Jan. 28, 2014

(54) ANALYTIC DEVICE WITH PHOTOVOLTAIC POWER SOURCE

(75) Inventors: Martin Vana, Mountain View, CA (US); William Dale Case, Tracy, CA (US)

(73) Assignee: Dionex Corporation, Sunnyvale, CA (US)

( * ) Notice: Subject to any disclaimer, the term of this patent is extended or adjusted under 35 U.S.C. 154(b) by 683 days.

(21) Appl. No.: 12/714,411

(22) Filed: Feb. 26, 2010

(65) Prior Publication Data

US 2011/0210718 A1 Sep. 1, 2011

(51) Int. Cl.
G01N 27/403 (2006.01)

(52) U.S. Cl.
USPC ........... 204/406; 324/107; 323/238; 323/266; 136/244; 136/246; 204/408; 422/68.1

(58) Field of Classification Search
USPC ......................................................... 324/107
See application file for complete search history.

(56) References Cited

U.S. PATENT DOCUMENTS

| | | | | |
|---|---|---|---|---|
| 3,952,242 A * | 4/1976 | Ukai | ............................. | 323/238 |
| 4,404,065 A | 9/1983 | Matson | | |
| 4,423,478 A * | 12/1983 | Bullock et al. | .................. | 363/89 |
| 5,368,706 A | 11/1994 | Bowers et al. | | |
| 5,757,170 A * | 5/1998 | Pinney | ........................... | 323/266 |
| 6,203,758 B1 * | 3/2001 | Marks et al. | .................. | 422/68.1 |
| 6,263,002 B1 * | 7/2001 | Hsu et al. | ........................... | 372/6 |
| 6,549,687 B1 * | 4/2003 | Kochergin et al. | ............. | 385/12 |
| 6,572,748 B1 | 6/2003 | Herrmann et al. | | |
| 7,638,750 B2 * | 12/2009 | Kline | ......................... | 250/214 R |
| 2002/0046763 A1 * | 4/2002 | Berrios et al. | ................. | 136/244 |
| 2002/0130636 A1 * | 9/2002 | Yokokura et al. | .............. | 320/122 |
| 2005/0012543 A1 | 1/2005 | Stearns et al. | | |
| 2005/0194955 A1 * | 9/2005 | Moran | ........................... | 323/315 |
| 2006/0267913 A1 * | 11/2006 | Mochizuki et al. | ............ | 345/100 |
| 2007/0012349 A1 | 1/2007 | Gaudiana et al. | | |
| 2008/0264148 A1 | 10/2008 | Bulst et al. | | |
| 2010/0206355 A1 * | 8/2010 | Johnson | ........................ | 136/246 |
| 2010/0277722 A1 * | 11/2010 | Kraiczek et al. | .............. | 356/244 |

OTHER PUBLICATIONS

Dionex ED50 Electrochemical Detector Operator's Manual, Document No. 031673, Revision 1, Apr. 2000, © 2000 Dionex Corporation.*

Toshiba Part No. TLP591 B Photocoupler GaAlAs Ired and Photo-Diode Array Datasheet, Toshiba Corp., Dated Dec. 9, 2008.*

"ED50A Electrochemical Detector Operator's Manual," rev. 02, Nov. 2002, pp. 2-15 to 2-18, 5-7 to 5-18, B17 to B28, Dionex Corporation (available at http://www.dionex.com/en-us/webdocs/57752-31772_02_ED50A_V17.pdf).

(Continued)

*Primary Examiner* — Benjamin M Baldridge
(74) *Attorney, Agent, or Firm* — Victor Johnson

(57) ABSTRACT

An analytical device including a sensor, an analytical circuit, and a power source. The power source includes an optical coupler formed of a light source and a photovoltaic cell for producing an electromotive force in response to light from the light source. The optical coupler is configured to provide the electromotive force to the analytical circuit. The power source may be configured for separation between the power supply and the resulting electromotive force supplied to the analytical circuit. Various aspects of the invention are directed to providing a power source for one or more components of an electrochemical detector. A method of providing power to an analytical instrument is also disclosed.

21 Claims, 3 Drawing Sheets

(56) References Cited

OTHER PUBLICATIONS

Bohs et al., "The UniJet: A New Electrochemical Detector for Microbore Liquid Chromatography," Current Separations, 1994, vol. 12, pp. 181-186.

Bowers, "A new analytical cell for carbohydrate analysis with a maintenance-free reference electrode," J. Pharmaceutical & Biomedical Anal., 1991, vol. 9, Nos. 10-12, pp. 1133-1137.

Dobson et al., "Plateau Potentials of the α+βPalladium Hydride Electrode at Temperatures between 25 and 195° C," J. Chem. Soc., Faraday Trans. 1, 1972, vol. 68, pp. 764-772.

Dobson et al., "Some Experimental Factors which Govern the Potential of the Palladium Hydride Electrode at 25 to 195° C," J. Chem. Soc., Faraday Trans. 1, 1972, vol. 68, pp. 749-763.

Dobson, "The PallapHode Electrode System," Platinum Metals Rev., 1981), vol. 25, No. 2, pp. 72-73.

Fleischmann et al., "A palladium-hydrogen probe electrode for use as a microreference electrode," J. Scientific Instruments, 1968, series 2, vol. 1, pp. 667-668.

Giner, J., "A Practical Reference Electrode," Electrochem. Soc., 1964, vol. 111, p. 376.

Goffe et al., "Internally charged palladium hydride reference electrode-Part 1: The effect of charging current density on long-term stability," Medical & Biological Engineering & Computing, 1978, vol. 16, pp. 670-676.

Ives et al., Reference Electrodes Theory and Practice, 1961, p. 111, Academic Press, New York.

Kelly et al., "Internally charged palladium hydride reference electrode: II Automatically controlled palladium hydride electrode," Medical & Biological Engineering & Computing, 1981, vol. 19, pp. 333-339.

Lunte et al, "Difference Mode Detection with Thin-Layer Dual-Electrode Liquid Chromatography/Electrochemistry," Anal. Chem., 1985, vol. 57, pp. 1541-1546.

Munasiri et al., "Palladium-hydrogen electrodes for coulometric titration analysis of acids and bases," J. Electroanal. Chem., 1992, vol. 332, pp. 333-337.

Otterson et al., "Absorption of Hydrogen by Palladium up to Hydrogen-Palladium Atom Ratios of 0.97," 1969, p. 1-15, NASA, Washington, DC.

Sawyer et al., "Experimental electrochemistry for chemists," 1974, p. 34, Wiley, New York.

Schwing et al., "Comparison of Different Palladium-Hydrogen Electrode As pH Indicators," Analytica Chimica Acta, 1956, vol. 15, pp. 379-388.

Stock et al., "The Palladium Electrode in Aqueous and Non-Aqueous Titrimetry," Analytica Chimica Acta, 1959, vol. 20, pp. 73-78.

Welch et al., "Comparison of Pulsed Coulometric Detection and Potential-Sweep Pulsed Coulometric Detection for Underivatized Amino Acids in Liquid Chromatography," Anal. Chem., 1989, vol. 61, pp. 555-559.

* cited by examiner

ANALYTIC DEVICE WITH PHOTOVOLTAIC POWER SOURCE

BACKGROUND OF THE INVENTION

1. Field of the Invention

This invention relates, in general, to an analytic device including a power source.

2. Description of Related Art

Modern analytic systems are typically powered by electrical current and voltage. Although subcomponents of the system may be powered with a primary system power, the power must be transformed for each component to a desired voltage or current. Some components require a regulated current or voltage at very low levels, within a narrow variation range, and/or with low noise, which can be difficult to produce based on the primary system power.

In the fields of biochemistry and analytical chemistry, laboratory researchers sometimes analyze samples based on small differences in electrochemical responses. For this reason, electrochemical detectors generally require a fixed, low-power input and exhibit a high sensitivity to minute fluctuations and variations in electrical current or voltage. An electrochemical detector may employ a reference electrode combination operated by application of a biasing potential. The bias voltage is applied between the two electrodes where one of the electrodes carries the output signal of the electrochemistry detector. In turn, the detector is connected to a recording device that provides a permanent record of the events which have taken place at the active surface of the detector.

A significant problem in biomedical and biochemical investigations is the ability to monitor the minute amounts (e.g. picogram, or femtogram level) of biologically active compounds. This translates into a need for analytic systems with sufficient sensitivity for the target compounds, linearity over the physiologically relevant concentration range, and compatibility with the rest of the system components. The system generally requires a fixed and accurate power supply. Even minor variations from the desired voltage can cause drastic performance errors.

Another important concern with sensitive electrical equipment is the reduction or elimination of noise attributed to the power supply. In the example of detector electrodes, noise can be especially troublesome. The detector electrodes represent relatively high impedance, which mandate particularly high insulation of the biasing power supply in order to maintain sufficient noise performance. By contrast, other research components are typically powered by high voltage and are relatively insensitive to noise and voltage fluctuations. A problem occurs when the high power source introduces noise to more sensitive components. Small variations, errors, and noise from the power supply can cause large errors in the accuracy of the device and system. Greater variations in the power supply output consequently limit the sensitivity of the powered device.

One method of powering electrochemical detectors is with a conventional AC power supply. An AC power supply is typically used in combination with a transformer to convert the system power to a fixed biasing voltage for the detectors. AC power supplies, however, inherently produce noise and thus are unsuitable for sensitive electrical components.

Another method of powering electrochemical detectors is with a conventional DC/DC power supply. Similar to AC power supplies, a conventional DC/DC power supply typically injects a significant level of switching signal noise into the sensor circuit. Similar problems are observed when a DC/DC power supply is employed to power a front-end amplifier stage connected to floating electrodes. Good insulation and power noise separation is required for effective operation. It has been found that a conventional DC/DC power supply generally provides unacceptable errors in the biasing voltage and/or injects too much noise into the system when powering sensitive equipment like electrochemical detectors.

In addition, especially in fluid environments, conventional power supplies present the problem of how to ground the devices without cross-talk. In some cases, such as when working with flammable compounds, the wiring and open contacts of traditional power sources even present safety hazards.

Another method for powering system components employs a separate and self-contained power source, such as a standard battery. Standard electrochemical batteries reduce the risk of introducing noise to the system. But batteries present several drawbacks. For one, users prefer that the system only use one power source. Preferably the system is plugged into a constantly available power source such as an electrical outlet. Batteries also present their own unique problems like slow discharge and the need for manual replacement. The system typically has to be designed to account for electrical drift as the battery ages. Batteries also take up space, which can be problematic for some applications. Additionally, batteries can not be turned on and off.

In light of the foregoing, it would be beneficial to have methods and apparatuses which overcome the above and other disadvantages of known power supplies.

It would be beneficial to provide a power supply that can provide small voltages within a range sufficient for highly sensitive equipment. It would be beneficial to provide an improved power supply for use with biomedical and biochemical testing and analytical equipment.

It would be beneficial to provide a power supply that provides a constant and accurate current or voltage. It would be beneficial to provide a power supply with minimal noise. It would be beneficial to provide a method and device for providing a consistent, insulated voltage or current.

It would be beneficial to provide a power supply that integrates with existing systems and does not require a separate power connection. It would be beneficial to provide a power supply that reduces or eliminates grounding problems. It would be beneficial to provide a power supply that is floating and can be provided in different parts of an electrical system. It would be beneficial to provide a power supply that can be turned on and off.

It would be beneficial to provide a power source integrated with an analytical detector.

These and other advantages are provided by the devices and methods of the present invention.

BRIEF SUMMARY OF THE INVENTION

In summary, one aspect of the present invention is directed to an analytical device including a sensor, an analytical circuit, and a power source. The power source includes an optical coupler having a light source activated by electrical power and a photovoltaic cell for producing an electromotive force in response to light from the light source. The optical coupler is configured to provide the electromotive force to the analytical circuit.

In various embodiments, the electromotive force is current. In various embodiments, the electromotive force is voltage. In various embodiments, the voltage is an insulated voltage.

In various embodiments, the output voltage is less than 3 V. In various embodiments, the voltage is between about 1.25 V and about 2 V. In various embodiments, the voltage is between about 1.5 V and about 1.7 V. In various embodiments, the voltage is about 1.6 V. In various embodiments, the voltage is about 1.601 V to about 1.608 V.

In various embodiments, the voltage is substantially constant within a narrow variation range. In various embodiments, the voltage fluctuates within a range of about +/−3 mV. In various embodiments, the voltage fluctuates within a range of about +/−16 microvolts. In various embodiments, the voltage fluctuates within a range of about +/−0.7 microvolts. In various embodiments, the voltage fluctuates within a range of about +/−0.05% of the desired voltage. In various embodiments, the voltage fluctuates within a range of about +/−0.01% of the desired voltage.

In various embodiments, the noise level is less than 125 dB. In various embodiments, the noise level of the output voltage is less than approximately 50 dB. In various embodiments, the noise level of the output voltage is less than about 100 dB.

In various embodiments, the voltage is substantially consistent and yields a current representing charge rate variation of about +/−0.5 micro Coulombs/s or less. In various embodiments, the voltage is substantially consistent and yields a current representing charge rate variation of about +/−20 pico Coulombs/s. In various embodiments, the voltage is substantially consistent and yields a current representing charge rate variation of about +/−6 pico Coulombs/s.

In various embodiments, the output current is less than about 1 mA. In various embodiments, the output current is less than about 30 microamps. In various embodiments, the output current is less than about 1.5 microamps. In various embodiments, the output current is substantially constant within a narrow variation range. In various embodiments, the current fluctuates within a range of about +/−0.5 microamps. In various embodiments, the current fluctuates within a range of about +/−20 picoamps. In various embodiments, the current fluctuates within a range of about +/−6 picoamps.

In various embodiments, the optical coupler includes an insulation boundary between the light source and the photovoltaic cell. In various embodiments, the insulation boundary is a separation distance sufficient to electrically decouple the light source and the photovoltaic cell. The output section of the power supply may be insulated from the rest of the instrument providing power to the light source by the insulation boundary. In various embodiments the insulation resistance across the insulation boundary is about 10 MOhm. In various embodiments the insulation resistance across the insulation boundary is about 10 TOhm. In various embodiments the capacitance across the insulation boundary is less than about 10 pF. In various embodiments the capacitance across the insulation boundary is less than about 1 pF.

In various embodiments, the power source further includes a power supply for providing the electrical power and a controller for controlling the power supply.

In various embodiments, the light source and photovoltaic cell are optically coupled by one of a gap, a lens, a mirror, a fiber optic member, and a combination of the same.

In various embodiments, the analytical circuit includes a regulator for conditioning the electromotive force from the photovoltaic cell. The analytical circuit may include a pre-regulator between the PV cell and the regulator. In various embodiments, the analytical circuit includes an amplifier.

In various embodiments, the sensor is configured for performing electrochemical analysis of a sample. The coupler may be connected directly to the sensor. In various embodiments, the sensor includes a reference electrode. In various embodiments, the sensor is an electrochemical detector.

Various aspects of the present invention are directed to an analytical instrument with the above analytical device and power source. Various aspects of the present invention are directed to a chromatography system including the above analytical instrument.

Various aspects of the present invention are directed to a method of analyzing a sample including providing electrical power from a power source, converting the electrical power into a light signal, converting the light signal into an electromotive force, and powering an electrode of an analytical device with the electromotive force for analytical detection of a sample within the device. In various embodiments, the method includes measuring an electrochemical response from a sample in contact with the electrode.

The devices and methods of the present invention(s) have other features and advantages which will be apparent from or are set forth in more detail in the accompanying drawings, which are incorporated in and form a part of this specification, and the following Detailed Description of the Invention, which together serve to explain the principles of the present invention(s).

DETAILED DESCRIPTION OF THE INVENTION

Figure 1:
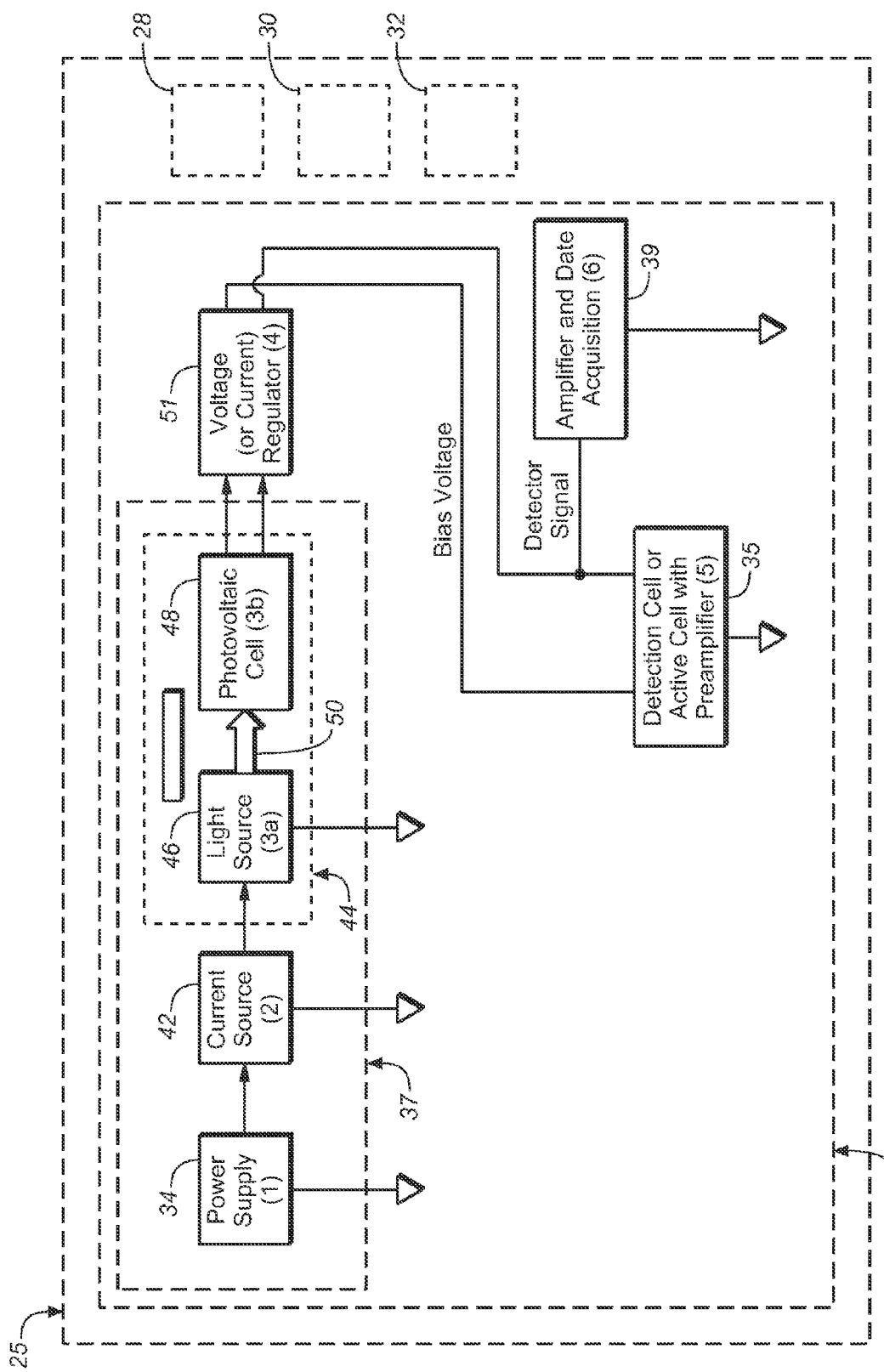
FIG. 1 is a block diagram of an exemplary chromatography system including an analytical device having a power source for a detection cell in accordance with the present invention.
Figure 2:
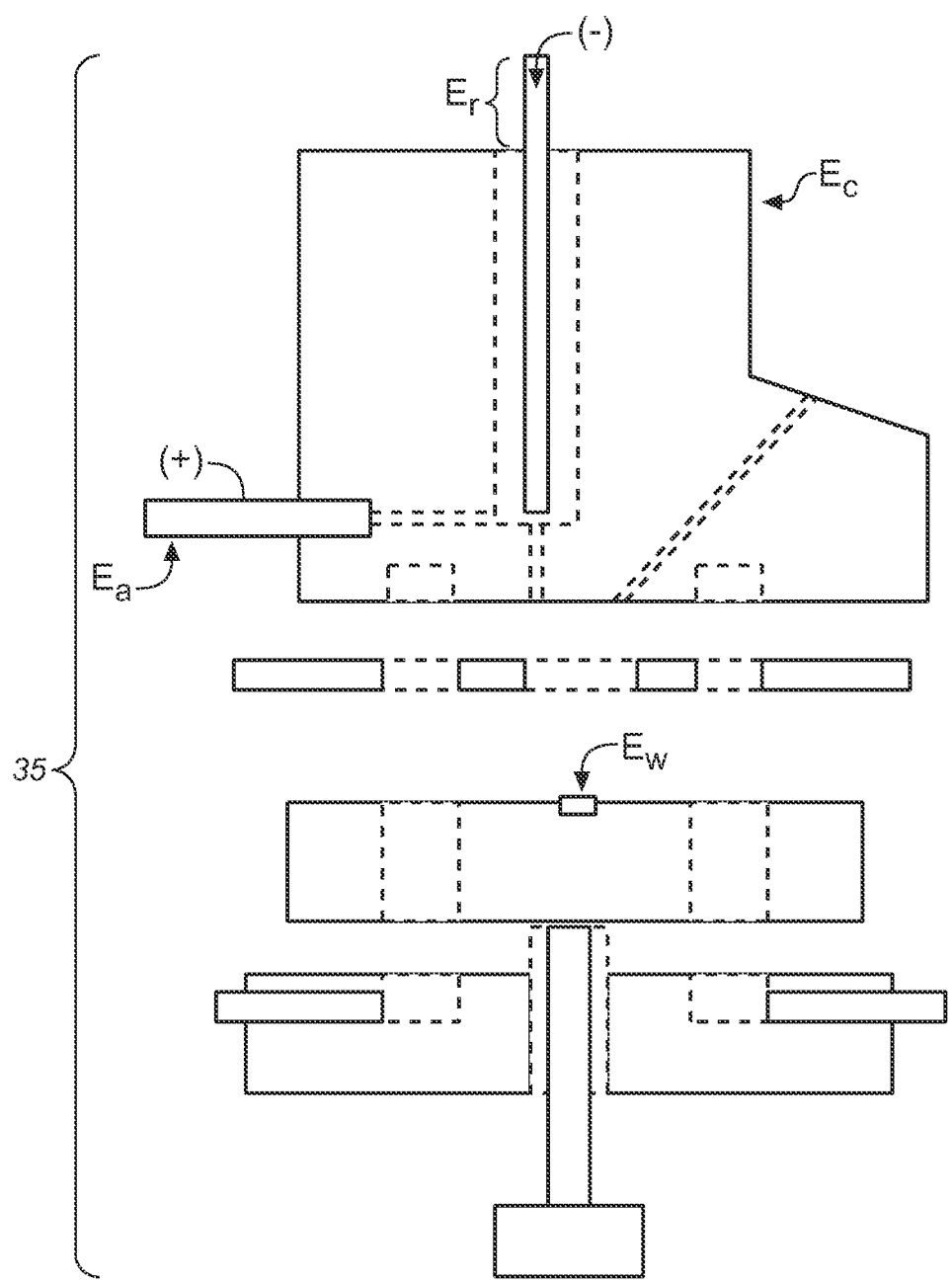
FIG. 2 is an enlarged schematic view of an exemplary detection cell of the system of FIG. 1.

Reference will now be made in detail to the various embodiments of the invention, examples of which are illustrated in the accompanying drawings. While the invention will be described in conjunction with the various embodiments, it will be understood that they are not intended to limit the invention to those embodiments. On the contrary, the invention is intended to cover alternatives, modifications and equivalents, which may be included within the spirit and scope of the invention as defined by the appended claims.

Attention is directed to the drawings where like components are designated by like reference numerals throughout the various figures.

FIG. 1 illustrates an exemplary system for biochemical analysis. The exemplary system, generally designated 25, is an ion chromatography system. Various aspects of the system are similar to those in the UltiMate® 3000 HPLC and RSLC systems, the ICS-3000, and the ICS-5000 DC marketed by Dionex Corporation of Sunnyvale, Calif.

The system includes an analytical device, generally designated 27, among other components. The exemplary system is an ion chromatography system that includes analytical device 27, injector 28, column 30, and pumps 32.

A power supply 34 provides the primary input power to the intended instrument. Analytical device 27 includes a sensor, generally designated 35, a power source 37, and an analytical circuit, generally designated 39 (FIG. 1). In various embodiments, sensor 35 is a detector. The analytical circuit and sensor may be an integrated unit or discrete and separate components.

The exemplary sensor is a multi-electrode detection cell. The detector cell includes a reference electrode $E_r$, working electrode $E_w$, counter electrode $E_c$, and auxiliary electrode $E_a$. Various aspects of the analytic device and sensor are similar to the device described in U.S. application Ser. No. 12/703,668, filed Feb. 10, 2010, and entitled ELECTROCHEMICAL DETECTION CELL FOR LIQUID CHROMATOGRAPHY SYSTEM, which is incorporated herein for all purposes by reference. Many of the parts of the device and sensor are similar to those found in the PED, ED50, and ED detectors marked by Dionex Corporation of Sunnyvale, Calif.

As shown in FIG. 1, the primary power may come from any conventional source outside of the instrument. In various embodiments, the primary power comes from another component or a power supply 34 of the system. The primary power may also be provided by a charged battery. The primary supply power does not form a part of the present invention.

Figure 3:
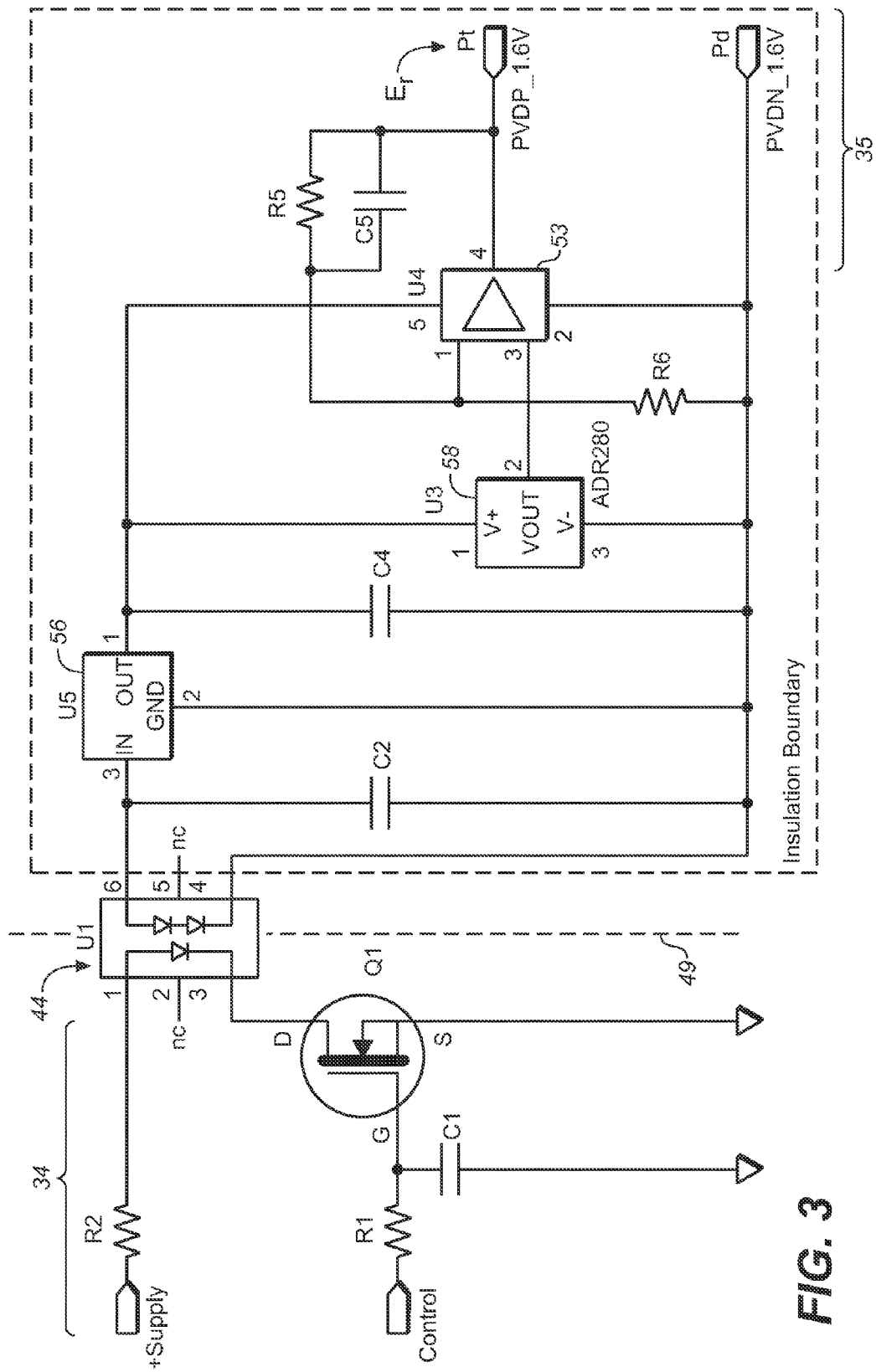
FIG. 3 is a circuit diagram of a portion of the exemplary analytical device of FIG. 1, illustrating the power source and analytical circuit connected to a reference electrode.

The primary power from power supply 34 is fed to a current source 42. In turn, the current source powers an optical coupler, generally designated 44. The optical coupler includes a light source 46 and photovoltaic (PV) cell 48. In various embodiments, an insulation boundary 49 is provided between the light source and photovoltaic cell as shown in FIG. 3. The optical coupler is connected to analytical circuit 39 as shown in FIG. 1.

Referring back to FIG. 1, optical coupler 44 is configured to provide an electromotive force to the exemplary detection cell electrodes. Light source 46 is activated by electrical power from current source 42 to provide a light signal. The light signal is transmitted to PV cell 48. The PV cell is configured to produce an electromotive force in response to the light signal from the light source.

In various embodiments, an appropriate constant DC voltage level powers the current source to drive light source 46 as a part of the optical coupler 44. Analytical device 27 optionally includes a controller for controlling current source 42. The controller may produce a signal to enable or disable analytical device 27 or to change the amount of power transmitted to insulated portion (shown in FIG. 3) of the power supply and electrodes of the detection cell 35, if needed.

Various aspects of optical coupler 44 are similar to those of the TLP591B Photocoupler (GaAlAs Ired & Photo-Diode Array) and the TLP190B Photocoupler (GaAlAs Ired & Photo-Diode Array), both sold by Toshiba Corporation of Tokyo, Japan. Various aspects of the optical coupler are similar to the 4V Output Solar Cell, Model No. CPC1824, sold by Clare of Milpitas, Calif. In some respects, the optical coupler may be sourced from common parts. The optical coupler may be formed of a LED light source illuminating a semiconductor photovoltaic cell (or cells) as a source of electromotive force (emf). In various embodiments, the PV cell is a standard photodiode. One will appreciate that the PV cell may be formed of any number of devices and configurations for converting the light signal of the light source into an electromotive force.

In various embodiments, the light source and PV cell are single, distinct parts in direct contact such that there is a fixed optical and mechanical path through the optical coupler. The light source and PV cell may be coupled through a homogenous metal contact. Good coupling between the light source and PV may reduce the need to account for temperature variations and other factors. Light source 46 and PV cell 48 are optically coupled by a coupling device 50. Coupling device 50 is generally configured to transfer and/or collimate light from the light source onto the PV cell. The coupling device may be a physical gap, a lens, a mirror, a fiber optic device, and/or other suitable means.

Optical coupler 44 can constitute a discrete light source and PV cell placed in proximity to each other or connected through an optics system for conveying the light between the source and PV cell. A variety of optical coupler components are available on the market where both the light source and PV cell(s) are located in a common housing. These components are commonly used in power electronics for switching of MOS FET and IGBT transistors while maintaining the control circuitry at a different reference potential.

Because the optical coupler converts electrical current from current source 42 to a light signal, the inherent risk of transmitting electrical noise in the coupler is significantly minimized. The coupling between light source 46 and PV cell 48 is generally limited to the light signal; the light source and PV cell are electrically insulated from each other. Thus, the optical coupler inherently provides for good electrical insulation without complicated shielding and the like.

Light source 46 and PV cell 48 are optionally separated by an actual insulation boundary 49. The insulation boundary may be a physical object or a separation distance sufficient to decouple or reduce interference between the devices. The exemplary separation distance is approximately 1 mm. One will appreciate that other distances may be employed depending on the desired dielectric strength and other parameters. One will appreciate that a mechanical or physical separation distance may not be necessary or may be minimal because the light source and PV cells are functionally insulated.

Optical coupler 44 outputs an electromotive force in response to the current input from current source 42. The electromotive force from the optical coupler, via PV cell 48, is connected to the instrument to be powered. In various embodiments, the electromotive force is a biasing voltage to be applied to an electrochemical detector.

In the exemplary embodiment, the optical coupler is connected directly to an electrode pair of the device through regulator 51. The regulator circuit may be formed as part of the instrument to be powered or may be separate from the operative elements of the device.

In various embodiments, device 27 is an instrument for performing electrochemical analysis of a sample. In various embodiments, the sensor includes a reference electrode. In various embodiments, the sensor is an electrochemical detector. The electrochemical detector may be a high impedance detector.

In various embodiments, the analytical circuit includes a regulator 51 for conditioning the electromotive force from PV cell 48 before it is applied to sensor 35. Resulting voltage from the optical coupler may be further conditioned, regulated and/or filtered, in optional regulator 51. The regulator receives the electromotive force from the optical coupler and transforms it into the desired current or voltage characteristics.

The PV cell and regulator generally constitute a secondary power supply system or circuit. Output current or voltage from the regulator is well insulated from the primary supply system constituting power supply 34, current source 42, and light source 46. Therefore, the secondary circuit can be connected directly to the high impedance output of sensor 35 without significantly affecting the sensor output signal.

Sensor 35 is connected to a data acquisition (measurement) unit 55. Measurement unit 55 may consist of a high input impedance amplifier, signal conditioner, and Analog-to-Digital converter to quantify the measured signal from the sensor.

FIG. 3 is a schematic diagram of the sensor instrument 27 including a power source in accordance with the present invention. The exemplary power source is configured as a voltage regulator for providing a specific voltage to the sensor. One will appreciate from the description herein that the power source may be configured as a current regulator. One will also appreciate that the components may be varied and adjusted depending on the application requirements.

The exemplary detection instrument includes power source 37 connected to a reference electrode $E_r$ of a detector. The exemplary power source is split into two general portions separated by insulation boundary 49. In the secondary portion, power is received from the primary (emitter) circuit by the photovoltaic cell of the optical coupler. In the second circuit, the output from the optical coupler is supplied to a regulator 51, which in turn powers the exemplary sensor electrode. In various embodiments, regulator 51 includes two stages generally depicted as element 56 for the first stage and elements 53 and 58 together with C5, R5, and R6 for the second stage. In various embodiments, the regulator includes a single stage. One will appreciate that the regulator may include three or more stages, or the regulator may be omitted. The one or more stages together, in general, may be viewed as a "voltage regulator."

Resistor R2 represents the current source 42 that is input to light source 46 of optical coupler 44. The exemplary optical coupler utilizes a light emitting diode (LED) as the light source. The transistor Q1 is configured to control (e.g. enable or disable) the current source thereby controlling the circuit.

The optical coupler provides an insulation boundary between the supply power and analytical detection circuit and regulates voltage to the instrument. In various embodiments, the optical coupler includes two or more light sources. In various embodiments, the optical coupler includes two or more PV cells. In various embodiments, the light source and PV cells are formed as a single, unitary component or housed within a single housing. The number and configuration of the light sources and PV cells may vary depending on the application.

In various embodiments, the power supplied by the current source is controlled or modulated by controlling the light intensity of the light source. The intensity of the light source consequently controls the resulting voltage from the PV cell. Thus, the optical coupler allows for regulation of the supplied current without the typical problems attendant with conventional systems such as noise interference and voltage fluctuations.

As will be appreciated from the description herein, the optical coupler can be connected directly to the instrument to be powered. Alternatively, the electromotive force generated by the optical coupler may be modified or regulated. Direct connection refers to direct contact without the use of intermediary devices and/or wires. In various embodiments, the power source and analytical circuit are housed on a single support. The optical coupler may be mounted on a circuit board and connected to an integrated circuit.

In the exemplary analytical device, secondary photo-electric voltage generated by the PV cell 48 is pre-regulated in an optional three-point pre-regulator 56. One will appreciate that the use of pre-regulator 56 depends on the application. The pre-regulator limits the influence of voltage variations on the final low-noise regulator stage. The pre-regulator also protects the final regulator 51, which may not withstand maximal no-load optical coupler voltage.

As described above, optical coupler 44 provides an electrically insulated output voltage or current. The optical coupler, however, may introduce a small amount of noise into the system. To that end, device 27 may be configured with means to reject downstream electrical noise. The exemplary device includes an optional precision, low-quiescent current voltage reference 58 and optional device 53. The operational amplifier gain is defined by the combination of feedback resistors R5 and R6 to provide a desired biasing voltage at the output. In various embodiments, the reference and amplifier serve to filter noise before the voltage or current is applied to the reference electrodes. Optional regulator 51 may also be configured to reject noise from the optical coupler. One of ordinary skill in the art will appreciate from the description herein how to adjust the reference and amplifier to suit the particular device application.

The exemplary device powers a reference electrode $E_r$ for an analytical detector. A single Pt—Pd electrode is connected downstream from the amplifier. The power source in accordance with the present may also apply a voltage or current to a working electrode. One will appreciate from the description herein that various modifications may be made to the system in accordance with the present invention. Two or more electrodes may be powered by a single power source. The device may include a plurality of electrodes, in various configurations, each powered by a separate floating power source.

The optical coupler and power source described above can be configured to provide a voltage to a variety of instruments in the system. In various embodiments, instead of driving of a biasing electrode in a detection cell, the power source is configured as a floating power source to provide power to a preamplifier or an entire sensor circuit. The sensor circuit may also have its output signal galvanically-insulated and provide the output signal through optical insulation such as a fiber link or RF transmitter.

The downward facing arrows in FIG. 3 represent connections to the reference ground. In various embodiments, the optical coupler is referenced to the instrument (sensor) signal instead of the common system ground. Rather than a common ground, the power source and optical coupler are floating and provide a relative voltage that is maintained at the same potential irrespective of where it is positioned in the overall system. In this manner the power source is "floating" and may be used as at various locations where a reference voltage or current is needed.

In operation and use, current from a conventional power supply circuit is input to light source 46 of optical coupler 44. Transfer of the electrical power between the supply source and the instrument is performed by converting the electricity into light in light source 46 of the optical coupler.

The light is then converted back into an electromotive force (emf). This emf is functionally (electrically) insulated from the primary electrical power supply circuit providing power for the light source. The insulation (AC and DC coupling) between the primary and secondary circuits can thus be reduced or virtually eliminated. Therefore, the output voltage or current may be used to create electrode bias or drive circuits directly connected to measured signal originated at a high impedance source like an electrochemical detection cell. This conversion principle generally does not rely on employing of an Alternating Current (AC) as would be common in an existing implementation employing a transformer.

The output from the optical coupler may be controlled by the current source applied to the light source thereby controlling the light intensity. One will appreciate, however, that the electromotive force output by the optical coupler may be based on several factors aside from the light intensity. The current or voltage output from the optical coupler may be determined as a function of other properties including, but not limited to, temperature, conductivity, voltage at an additional detector cell terminal, and other factors.

The electromotive force from the optical coupler is used to power the exemplary sensor 35. In various embodiments, the electromotive force is a voltage applied to the detector electrodes under sufficient conditions for detection and/or analysis of a target analyte in a sample. One will appreciate from the description herein that the device in accordance with the present invention provides a voltage or current that is both accurate and insulated. By "insulated" it is meant that the output circuit potential may vary relative to the input power (e.g. the system supply power to the optical coupler light source) without affecting the circuit. Further, the power supplied to the exemplary detector electrodes is not tied to any common ground. In various embodiments the potential difference between the input and output (floating) circuit may be up to about 10 V. In various embodiments, the potential difference between the input and output (floating) circuit may be up to about 100 V.

The output section of the power supply is insulated from the rest of the instrument providing power to the light source by insulation boundary 49. In various embodiments the insulation resistance across insulation boundary 49 is about 10 MOhm. In various embodiments the insulation resistance across the insulation boundary 49 is about 10 TOhm. In various embodiments the capacitance across the insulation boundary 49 is less than about 10 pF. In various embodiments the capacitance across the insulation boundary 49 is less than about 1 pF.

In various embodiments, the voltage is less than 3 V. In various embodiments, the voltage is between about 1.25 V and about 2 V. In various embodiments, the voltage is between about 1.5 V and about 1.7 V. In various embodiments, the voltage is about 1.6 V. In various embodiments, the voltage is about 1.601 V to about 1.608 V. In various embodiments, the voltage is substantially constant within a narrow variation range. In various embodiments, the voltage fluctuates within a range of about +/−16 mV, preferably within a range of about +/−3 microvolts, and more preferably within a range of about +/−0.7 microvolts. In various embodiments, the voltage fluctuates within a range of about +/−0.05% of the desired voltage, and preferably within a range of about +/−0.01% of the desired voltage.

In various embodiments, the noise level of the output voltage is less than approximately 50 dB, preferably less than about 100 dB, and more preferably less than about 125 dB.

In various embodiments, the voltage is substantially consistent and yields a current representing charge rate variation of about +/−20 micro Coulombs/s or less, preferably yielding a current representing charge rate variation of about +/−6 pico Coulombs/s, and more preferably yielding a current representing charge rate variation of about +/−0.5 pico Coulombs/s.

In various embodiments, the output current is less than about 1 mA, preferably less than about 30 microamps, and more preferably less than about 1.5 microamps. In various embodiments, the output current is substantially constant within a narrow variation range. In various embodiments, the current fluctuates within a range of about +/−20 microamps, preferably within a range of about +/−6 picoamps, and more preferably within a range of about +/−0.5 picoamps.

The exemplary sensor generates an electrochemical signal based on the analysis operation. Measurement unit 55 is connected to the sensor for measuring and recording the output signal from the sensor.

In the above manner, the power source provides an electromotive force to the instrument to be powered while reducing the risk of negatively affecting the instrument performance. In the exemplary case of a sensor with a floating power source, the power source provides sufficient constant power to the sensor while maintaining noise below a level that significantly impairs or alters the sensor output signal measured by the measurement unit.

In various embodiments, the light source and PV cells of the optical coupler are in direct contact such that light from the light source is fed directly to the PV cell. In this case, the supplied current is fed to the optical coupler and directly converted by the optical coupler. This configuration can be beneficial in environments where it is desirable to reduce interaction with the environment, such as in fluidic environments. The resulting voltage from the optical coupler is optionally fed directly to the sensor instrument. The power source may be integrally formed with the instrument to be powered or may be separate and electrically connected.

The system and power source of the present invention has been found to provide many advantages over conventional power sources. The optical coupler can be designed with favorable emitter (primary) circuit and receiver (secondary) circuit separation, which provides for very good conductive and capacitive insulation of the input and output circuits. Because the system power supply is electrically isolated from the voltage supplied to the instrument, the noise in the analytical circuit is significantly reduced. The optical coupler also can be operated from a DC power source. This further reduces or eliminates noise (AC) injected into the supplied (secondary) circuit for the instrument. The reduction of noise in the system also enables the delivery of a more constant, sustainable, and accurate voltage and/or current.

The system also provides very good electromagnetic interference (EMI) immunity. The system design also does not have the problems of providing adequate grounding of the measurement and reference electrodes.

In comparison to conventional methods and devices, the system of the present invention can generally be manufactured from common parts at a reduced cost. The system is also compact and simple. The system also does not require large and cumbersome EMI shielding. Further, the power source requires little real estate on the printed circuit board (PCB).

While the invention has been described in terms of an analytical device for electrochemical analysis, one will appreciate from the foregoing that the device of the present invention may be employed to power a variety of electrical components.

EXAMPLES

The invention is further illustrated by the Examples that follow. The Examples are not intended to define or limit the scope of the invention.

Example 1

A power source in accordance with the above was implemented and tested as a biasing power supply for a Pt—Pd electrode in the ED module of an ICS-5000 DC system. The power supply was about 1.5 V to about 2.2 V, and generally about 2 V. The system was operated at 25 degrees Celsius.

The PV cell output was regulated down with a linear voltage regulator to maintain a stable level of about 1.6 V. The power source was enabled/disabled by means of switching the LED current on and off. The secondary (output) circuit of the PV cell together with the regulator was floating and referenced to the high impedance ED cell output signal.

The output voltage from the optical coupler was found to have excellent noise performance. This is believed to be due in large part to the DC principle of operation of the optical coupler and good primary to secondary separation. The power source was thus found to provide fixed and sustainable power to the sensor with minimal noise.

For convenience in explanation and accurate definition in the appended claims, relative terms such as "outside" are used to describe features of the present invention with reference to the positions of such features as displayed in the figures.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. An analytical device comprising:
   a sensor having at least one electrode;
   an analytical circuit comprising a regulator; and
   a power source including:
   an optical coupler having:
   a light source activated by electrical power; and
   a photovoltaic cell for producing an electromotive force in response to light from the light source;
   wherein the regulator of the analytical circuit receives the electromotive force from the optical coupler, conditions the electromotive force and provides a conditioned electromotive force to the sensor and powers the at least one electrode of the sensor of the analytical device, for analytical detection of a sample within the device, or measuring an electrochemical response from a sample in contact with the electrode, and
   wherein the regulator is electrically insulated from both the light source and the power source.

2. The device according to claim 1, wherein the electromotive force is a voltage.

3. The device according to claim 2, wherein the voltage is an insulated voltage.

4. The device according to claim 2, wherein the voltage is less than 3 V.

5. The device according to claim 4, wherein the voltage is substantially consistent and fluctuates within a range of about +/−3 mV.

6. The device according to claim 4, wherein a noise level of the voltage is more than 50 dB below the voltage.

7. The device according to claim 2, wherein the voltage is substantially consistent and yields a current representing charge rate variation of approximately +/−0.5 micro coulombs/s.

8. The device according to claim 1, wherein the electromotive force is current.

9. The device according to claim 1, wherein the optical coupler further includes an insulation boundary between the light source and the photovoltaic cell.

10. The device according to claim 9, wherein the insulation boundary is a separation distance sufficient to electrically decouple the light source and the photovoltaic cell.

11. The device according to claim 1, wherein the power source further includes:
    a power supply for providing the electrical power; and
    a controller for controlling the power supply.

12. The device according to claim 1, wherein the light source and photovoltaic cell are optically coupled by one of a gap, a lens, a mirror, a fiber optic member, and a combination of the same.

13. The device according to claim 1, wherein the sensor provides signals for performing electrochemical analysis of a sample.

14. The device according to claim 1, wherein the sensor includes a reference electrode.

15. The device according to claim 14, wherein the sensor is an electrochemical detector.

16. An analytical instrument comprising the analytical device of claim 1.

17. A chromatography system comprising the analytical device of claim 1.

18. A method of analyzing a sample with an analytical device, comprising:
    providing electrical power from a power source;
    converting the electrical power into a light signal with a light source;
    converting the light signal into an electromotive force;
    conditioning the electromotive force with a regulator, thereby producing a conditioned electromotive force, wherein the regulator is electrically insulated from both the power source and the light source; and
    powering an electrode of an analytical device with the conditioned electromotive force for analytical detection of a sample within the analytical device.

19. The method according to claim 18, further comprising:
    measuring an electrochemical response from a sample in contact with the electrode.

20. The device according to claim 1, wherein the regulator includes a first stage and a second stage.

21. The device according to claim 1, wherein the regulator includes a three-point pre-regulator.

* * * * *